(12) United States Patent
Zellhuber et al.

(10) Patent No.: US 10,919,821 B2
(45) Date of Patent: Feb. 16, 2021

(54) PROCESS AND PLANT FOR PRODUCING AN OLEFIN

(71) Applicant: LINDE AKTIENGESELLSCHAFT, Munich (DE)

(72) Inventors: Mathieu Zellhuber, Martinsried (DE); Martin Schubert, Munich (DE); Florian Winkler, Munich (DE); Andreas Meiswinkel, Rimsting (DE)

(73) Assignee: LINDE AKTIENGESELLSCHAFT, Munich (DE)

(*) Notice: Subject to any disclaimer, the term of this patent is extended or adjusted under 35 U.S.C. 154(b) by 0 days.

(21) Appl. No.: 16/472,418

(22) PCT Filed: Dec. 22, 2017

(86) PCT No.: PCT/EP2017/084341
§ 371 (c)(1),
(2) Date: Jun. 21, 2019

(87) PCT Pub. No.: WO2018/115418
PCT Pub. Date: Jun. 28, 2018

(65) Prior Publication Data
US 2019/0359544 A1    Nov. 28, 2019

(30) Foreign Application Priority Data

Dec. 22, 2016   (EP) .................................... 16206447

(51) Int. Cl.
*C07C 5/48*         (2006.01)
*C07C 11/04*        (2006.01)

(52) U.S. Cl.
CPC .............. *C07C 5/48* (2013.01); *C07C 11/04* (2013.01); *C07C 2523/22* (2013.01); *C07C 2523/28* (2013.01); *C07C 2527/057* (2013.01)

(58) Field of Classification Search
CPC ....... C07C 11/04; C07C 5/48; C07C 2523/22; C07C 2523/28; C07C 2523/648;
(Continued)

(56) References Cited

U.S. PATENT DOCUMENTS

2010/0256432 A1* 10/2010 Arnold ...................... C07C 5/48
585/655

FOREIGN PATENT DOCUMENTS

EP           2716622 A1   † 4/2014
WO   WO 2013148006 A1    10/2013

OTHER PUBLICATIONS

PCT/EP2017/084341 International Search Report and Written Opinion dated Apr. 11, 2018, 7 pages.
(Continued)

*Primary Examiner* — Sharon Pregler
(74) *Attorney, Agent, or Firm* — Lathrop GPM LLP (57) ABSTRACT

The invention relates to a process for producing an olefin in which a reaction input stream containing at least one paraffin, oxygen and water is formed and in which a portion of the paraffin and of the oxygen in the reaction input stream is converted into the olefin by oxidative dehydrogenation using a catalyst to obtain a process gas, wherein the process gas contains at least the unconverted portion of the paraffin and of the oxygen, the olefin and the water from the reaction input stream. It is provided that at least one parameter which indicates an activity of the catalyst is determined and that an amount of the water in the reaction input stream is adjusted on the basis of the at least one determined parameter. A corresponding plant (100) likewise forms part of the subject matter of the invention.

20 Claims, 2 Drawing Sheets

(58) Field of Classification Search
CPC .......... C07C 2523/656; C07C 2527/057; B01J 19/0046; B01J 19/242; B01J 19/245; B01J 19/2475; B01J 2219/24; B01J 23/002; B01J 23/28; B01J 23/755; B01J 23/847; B01J 27/0576; B01J 35/065; B01J 35/1009; B01J 35/1014
See application file for complete search history.

(56) References Cited

OTHER PUBLICATIONS

PCT/EP2017/084341 International Preliminary Report on Patentability dated Jun. 25, 2019, 14 pages.
Li, Zuebing, and Iglesia, Enrique. "Kinetics and Mechanism of Ethane Oxidation to Acetic Acid on Catalysts Based on Mo—V—Mb Oxides." J. Phys. Chem. C, vol. 112, pp. 15001-15008 (2008). Published on Web Aug. 29, 2008.†

* cited by examiner
† cited by third party

PROCESS AND PLANT FOR PRODUCING AN OLEFIN

The invention relates to a process for producing an olefin and a corresponding plant according to the preambles of the independent claims.

PRIOR ART

Oxidative dehydrogenation (ODH) of paraffins having two to four carbon atoms is known in principle. In ODH the recited paraffins are reacted with oxygen to afford inter alia the respective olefins and water.

ODH may be advantageous compared to established processes for producing olefins such as steamcracking or catalytic dehydrogenation. For instance, there is no thermodynamic equilibrium limitation on account of the exothermicity of the reactions involved. ODH may be performed at comparatively low reaction temperatures. Regeneration of the employed catalysts is in principle not necessary since the presence of oxygen allows an in situ regeneration. Finally, compared to steamcracking smaller amounts of worthless byproducts such as coke are formed.

For further details concerning ODH reference is made to the relevant technical literature, for example Ivars, F. and Lopez Nieto, J. M., Light Alkanes Oxidation: Targets Reached and Current Challenges, in: Duprez, D. and Cavani, F. (ed.), Handbook of Advanced Methods and Processes in Oxidation Catalysis: From Laboratory to Industry, London 2014: Imperial College Press, pages 767-834, or Gärtner, C. A. et al., Oxidative Dehydrogenation of Ethane: Common Principles and Mechanistic Aspects, Chem Cat Chem, vol. 5, no. 11, 2013, pages 3196 to 3217.

Particularly when using MoVNbTeOx catalysts under industrially relevant reaction conditions ODH forms significant amounts of the respective carboxylic acids of the employed paraffins at by-products. For economic plant operation, corresponding joint production of olefins and the respective carboxylic acids is generally necessary when using the described catalyst type. This applies in particular to the production of ethylene by ODH of ethane (ODH-E) which simultaneously forms acetic acid.

The invention is hereinbelow described in particular having regard to ODH of ethane (so-called ODH-E). However, the use of said invention is in principle possible and advantageous also for ODH of higher paraffins such as propane and butane.

In processes based on oxidative reactions such as ODH, in particular ODH-E, the exothermicity necessitates effective temperature control and removal of heat of reaction formed. The danger of thermal runaway must also be prevented at all times.

Furthermore, in addition to the desired target product (ethylene in the case of ODH-E) such reactions form further oxygen-containing species such as the mentioned carboxylic acids but also for example carbonyl compounds. At excessively high temperatures particularly the undesired formation of the byproducts carbon monoxide and carbon dioxide is promoted and it is therefore desirable to keep temperatures and temperature gradients within suitable limits.

US 2010/0256432 A1 and WO 2013/148006 A1 indicate that water vapor may be employed as a thermal moderator in ODH, i.e. that an increased amount of water vapor can prevent overheating and that by dilution with water vapor a nonflammable reaction input may be provided.

One of the substantial challenges in such processes is therefore controlling the exothermic reaction. This is conventionally effected by dilution of the reaction gas and/or suitable cooling of the reaction volume. The present invention has for its object to further improve the controllability of such processes based on ODH, in particular ODH-E, and to overcome the disadvantages of conventional processes.

DISCLOSURE OF THE INVENTION

Against this background, the present invention proposes a process for producing an olefin, in particular ethylene, and a corresponding plant having the features of the independent claims. Embodiments are in each case subject matter of the dependent claims and of the description which follows.

Material streams, gas mixtures etc. may in the context of the present usage of the terms be rich or poor in one or more components, wherein the indication "rich" may represent a content of not less than 95%, 96%, 97%, 98%, 99%, 99.5%, 99.9% or 99.99% and the indication "poor" may represent a content of not more than 5%, 4%, 3%, 2%, 1%, 0.5%, 0.1% or 0.01% on a molar, weight or volume basis. If a plurality of components are reported the indication "rich" or "poor" relates to the sum of all components. If reference is made for example to "oxygen" or "ethane", a pure gas or else a mixture rich in the respective component may be concerned.

The terms "pressure level" and "temperature level" are used hereinbelow to characterize pressures and temperatures, these being intended to express that pressures and temperatures need not be present in the form of exact pressure/temperature values. A pressure level or temperature level may for example be within ±1%, 5%, 10%, 20% or 50% of a mean value. A plurality of pressure and temperature levels may represent disjoint or overlapping ranges. The same pressure/temperature level may for example still be present even when pressures and temperatures have been reduced on account of transmission losses or cooling. Pressure levels reported here in bar are absolute pressures.

A "rectification column" is in the context of the present usage of the term a separating unit adapted for at least partly fractionating a substance mixture injected in gaseous or liquid form or in the form of a biphasic mixture having liquid and gaseous proportions, optionally also in the supercritical state, by rectification, i.e. respectively generating from the substance mixture pure substances or at least substance mixtures having different compositions. Rectification columns are typically configured as cylindrical metal containers provided with internals, for example separating trays or ordered or unordered packings. A rectification column comprises a bottoms evaporator. This is a device having a heat exchanger which is heated and which is adapted for heating a liquid fraction accumulating in the bottom of the rectification column, also known as bottoms liquid. By means of a bottoms evaporator a portion of the bottoms product is continuously evaporated and recycled in gaseous form into the separating region.

Advantages of the Invention

When using MoVNbTeOx catalysts for ODH, in particular for ODH-E, catalyst activity reduces over time when a gas mixture supplied to the respective reactor contains no water or only very little water. This has the result that when using non-aqueous diluents or in case of completely solvent-free reactor operation a constant operation over time without continual readjustment is not possible. In practice this means that the temperature in the reactor must be continually increased to maintain a constant conversion.

The term "conversion" is to be understood here as meaning the molar proportion of employed reactants, ethane in the case of ODH-E, which altogether reacts to afford primary products and byproducts. The adjustment of temperature in such a reactor is typically effected in the form of temperature control of the cooling medium, for example using a thermal oil or a salt melt.

As already intimated above, in addition to the desired target product (ethylene in the case of ODH-E) such reactions form further oxygen-containing species such as the mentioned carboxylic acids but also for example carbonyl compounds. Furthermore at excessively high temperatures particularly the undesired formation of the byproducts carbon monoxide and carbon dioxide is promoted. This is of course also the case when such a reactor is operated at increasingly high temperature to maintain conversion on account of the reducing catalyst activity. A temperature increase in the reactor is in other words typically accompanied by a loss of selectivity and in particular increased formation of carbon monoxide and carbon dioxide. It must in particular be noted that small changes in the average reactor temperature can result in markedly higher temperature changes locally and the system is accordingly very sensitive toward control interventions.

The control cost and complexity for such a control means is high. However, in addition the adaptations will also result in unavoidable shifts in the temperature profile above the catalyst bed which in the case of severely reducing activity and high coolant temperature also result in an increased risk of thermal runaway. Ultimately, catalyst operation will be severely time-limited i.e. upon reaching a certain threshold value the catalyst must be replaced or, as far as is even technically possible, must be regenerated in a suitable form. Temperature tracking moreover exhibits a certain sluggishness since in particular in the case of cooling media and salt melts the entire inventory of this medium—not inconsiderable in a large industrial scale process—must correspondingly be tracked by thermal engineering means.

The present invention is based on the observation that the catalyst activity may be controlled by a water addition into the reactor input stream. To this end a parameter describing the catalyst activity is determined, in particular repeatedly and under constant preset reaction conditions/process settings, and the water addition is adjusted on the basis of this parameter. In particular on the basis of the repeatedly determined at least one parameter an increase or decrease in catalyst activity, in particular over time, is determined. This may be effected for example by determining a trend from parameters determined consecutively over a certain period. If a change is observed whose magnitude is above a defined threshold value, countermeasures in the form of water addition of water removal may be deployed in reaction. The present invention thus also makes it possible to recognize such possibly critical conditions in advance and can therefore for example safely prevent a thermal runaway.

In this way at excessively high catalyst activity and thus excessively high temperatures in the reactor a thermal runaway of the reactor may be prevented by reducing or preventing water addition. Compared to the sluggish adapting of the cooling medium this may be effected very rapidly. Reducing the water addition is thus a particularly advantageous regulative in such a process. This may also be effected for example as the first step of a multistage control process in which in a second step the temperature of the cooling medium can be adapted with correspondingly slower reaction.

By contrast, in the context of the present invention, even when an excessively low catalyst activity is found, which is apparent for example from decreasing conversion, the activity may be increased again by a corresponding water addition. In this way the mentioned disadvantages of excessively high temperatures and/or excessively steep temperature gradients as are encountered in the previously elucidated conventional processes may be avoided. In particular in the context of the present invention the formation of undesired byproducts such as carbon monoxide and carbon dioxide over time and means for reactor operation may altogether be markedly reduced. The present invention thus provides a process with altogether higher selectivity.

In the context of the present invention the high control cost and complexity of such a conventional control means is furthermore reduced/avoided. In the context of the present invention the elucidated shifts in the temperature profile above the catalyst bed may be reduced. The risk of thermal runaway is in this way likewise reduced. The use time of a catalyst may be increased in the context of the present invention.

Altogether in the context of the present invention by adjustment of water addition into the reactor input stream a constant catalyst activity in the respectively desired range may be maintained, thus rendering such a process markedly more controllable compared to the known processes. The present invention by defined addition of water maintains a constant catalyst activity which results in markedly reduced control cost and complexity, improved catalyst uptime and a reduced risk of thermal runaway. This may be realized both at full load operation and at partial load operation (continuous operating points). At the same time the necessary temperature adaptations and changes are minimized.

The present invention further provides the advantage that it makes staged reactor shutdown possible. By means of a first de-escalation stage the activity of the catalyst may be instantaneously reduced by water removal without completely stopping the reaction however. This at least delays, if not completely heads off, a possible thermal runaway while simultaneously limiting flow variations in the subsequent separation part. This results in an increase in safety and plant availability (reduced risk of thermal runaway), simplified operation (increased reaction time for operating personnel) and increased lifetime of the apparatuses in the separation part (fewer load variations). This also results in a better exploitation of the catalyst since said catalyst through more stable plant operation will achieve a longer lifespan and also on account of easier readjustment may be operated in a larger operating window and in turn for longer.

Such a reactor is in particular operated in a specified operating range. The specification of the operating range proposed here and more particularly elucidated hereinbelow results decisively from detailed reaction kinetics measurements on an MoVNbTeOx catalyst in a laboratory reactor. In these ethane oxidation experiments the water content in the reaction input stream after a first dry operating time was initially instantaneously increased from 0 to 22 vol % and later instantaneously reduced back to 0 vol % as also elucidated in FIG. 2. It was apparent that after addition of water the catalyst activity (here in the form of ethane conversion) increases rapidly and in the further course further increases slightly. Upon removal of the water a rapid short-term drop in activity followed further by a continuous decrease is once again observed. These changes in the water content are accompanied by a simultaneous step change in selectivities. Upon addition of water the product selectivity is shifted virtually instantaneously toward more acetic acid and upon removal of the water toward more ethylene.

For the partial load behavior of such a reactor it is accordingly the case that even at partial load a sufficient (minimum) amount of water is retained in the feed. This is because it is conceivable in practice that under partial load (due to reduced availability of reactants or reduced requirement for product) especially the conversion is reduced. According to the prior art to date this would initially be effected especially by reduction of the reactor temperature as a result of which the exothermicity of the reaction is reduced and the addition of a diluent may no longer be absolutely necessary. However, the performance of the present invention is in particular characterized precisely by the fact that in this case too the reported minimum proportion of water in the feed is retained and thus even at partial load a continuous operating condition is present for which a reduction in catalyst activity would otherwise be harmful.

Conversely, the observed physical effect may in the context of this invention also be used for a staged reactor shutdown in the case of a "Temperature High" alarm. This event represents a non-continuous operation in which the water feed is reduced to below the reported threshold values and in extreme cases down to zero. In such a staged reactor shutdown in a first step the water feed to the reactor may be significantly reduced or completely stopped to achieve a reduction in the catalyst activity. This effects a very rapid reduction in the comparatively exothermic formation of acetic acid and the corresponding evolution of heat in the reactor.

The fact that the formation of acetic acid is markedly more exothermic than the reaction of ethane to give ethylene and water is exploited here. The corresponding reaction enthalpies are reported for the equations (1) and (2) which follow:

$$C_2H_6 + 0.5 O_2 \rightarrow C_2H_4 + H_2O, \Delta H^0{}_R = -105 \text{ kJ/mol} \quad (1)$$

$$C_2H_6 + 1.5 O_2 \rightarrow CH_3COOH + H_2O, \Delta H^0{}_R = -642 \text{ kJ/mol} \quad (2)$$

Nitrogen or another suitable diluent may simultaneously partly or completely replace the omitted amount of water. The amount of oxygen metered in may simultaneously also be reduced to keep constant the oxygen proportion in the process gas at the reactor outlet. While the reaction will continue, it will do so markedly more moderately and a stabilization of the reactor temperatures to a particular level can therefore be achieved without appreciable intervention into the temperature of a cooling medium. A more far-reaching shutdown of the reactor (for example closing down of the introduced reaction input stream) may be provided as an additional de-escalation stage.

The present invention proposes a process for producing an olefin, in particular ethylene, in which a reaction input stream containing at least one paraffin, in particular ethane, oxygen and water, is formed and in which a portion of the paraffin and of the oxygen in the reaction input stream is converted into the olefin by ODH, in particular by ODH-E, using a catalyst to obtain a process gas, wherein the process gas contains at least the unconverted portion of the paraffin and of the oxygen, the olefin and the water from the reaction input stream. As mentioned, the process gas may also contain an array of further components, in particular byproducts such as organic acids (in the case of ODH-E acetic acid in particular), carbon monoxide and carbon dioxide. Further components are for example gases exhibiting inert behavior in ODH, including classical inert gases such as nitrogen and/or noble gases but also gases exhibiting inert behavior such as methane.

A "reaction input stream" is in the context of the present usage of the term the entire gas mixture subjected to ODH. This may in particular also be supplied to the reactor(s) used in the form of separate material streams. For example a paraffin-containing material stream and an oxygen-containing material stream may be combined to afford a corresponding reaction input stream in the reactor(s) used or upstream of the reactor(s).

A "forming" of the reaction input stream may comprise any process engineering treatment such as compression, decompression, cooling or heating, or else separating-off of substreams, introduction of further material streams or a chemical reaction of components. In the context of the present invention the forming of the reaction input stream in particular comprises for example heating a material stream that is converted into the reaction input stream. In this heating, the so-called feed preheating, the reaction input stream may be brought to a temperature which allows startup of the ODH in a downstream reaction unit having one or more reactors.

According to the invention it is provided that at least one parameter which indicates an activity of the catalyst is determined and that an amount of the water in the reaction input stream is adjusted on the basis of the at least one determined parameter. The at least one parameter is determined in particular repeatedly and in particular under constant process settings. The at least one parameter may for example be continuously monitored or periodically determined, for example at regular time intervals, and when a divergence, in particular beyond a predetermined threshold value, is present or a trend in previous measured values is indicating such a direction, an adjustment in the amount of water may be undertaken.

The constant process settings may in particular comprise constant reaction input parameters, wherein "constant reaction input parameters" is to be understood as meaning in particular a constant composition, a constant pressure, a constant temperature and/or a constant input amount of the reaction input which is supplied to the reactor(s) used/the ODH per unit time and which results in a correspondingly constant catalyst space velocity.

Constant process settings may in particular also comprise a constant heat removal, i.e. an output of a cooling system assigned to one or more of the reactors used that is adjusted to a constant level. When a corresponding cooling system is adjusted to a constant level, an increased catalyst activity may in particular be recognized via a temperature increase in the reactor.

It will be appreciated that "constant" process settings may also lie within a certain tolerance range. This is generally the case because a totally exact adjustment, for example of a composition of the input stream or of the pressure or temperature thereof is typically not possible on account of technical realities such as tolerances in metering units or pressure and temperature senders. However, constant process settings do not comprise any intentional change, for example of the composition of the reaction input, but rather generally represent constant target specifications for such manipulated variables. The changes which occur over time during such a procedure and via which at least one parameter can be determined are therefore not attributable to the reaction input or to parameters thereof or to other process settings but depend in particular on the catalyst activity.

As previously mentioned, US 2010/0256432 A1 and WO 2013/148006 A1 indicate that water vapor may be employed as a thermal moderator or diluent in ODH. In other words these documents teach that excessive evolution of heat in the reactor may be prevented when a larger amount of water vapor is added into the reactor(s) used in the reaction input. Thus the proportion of water in the reaction input is in particular increased here for operating points with higher conversion. In these cases the increased metered addition of water, which is predetermined beforehand, makes it possible to avoid an excessive increase in the temperatures and the conversion in the reactor when for example the average temperature in the catalyst bed is increased through a change in the cooling system settings.

Figure 2:
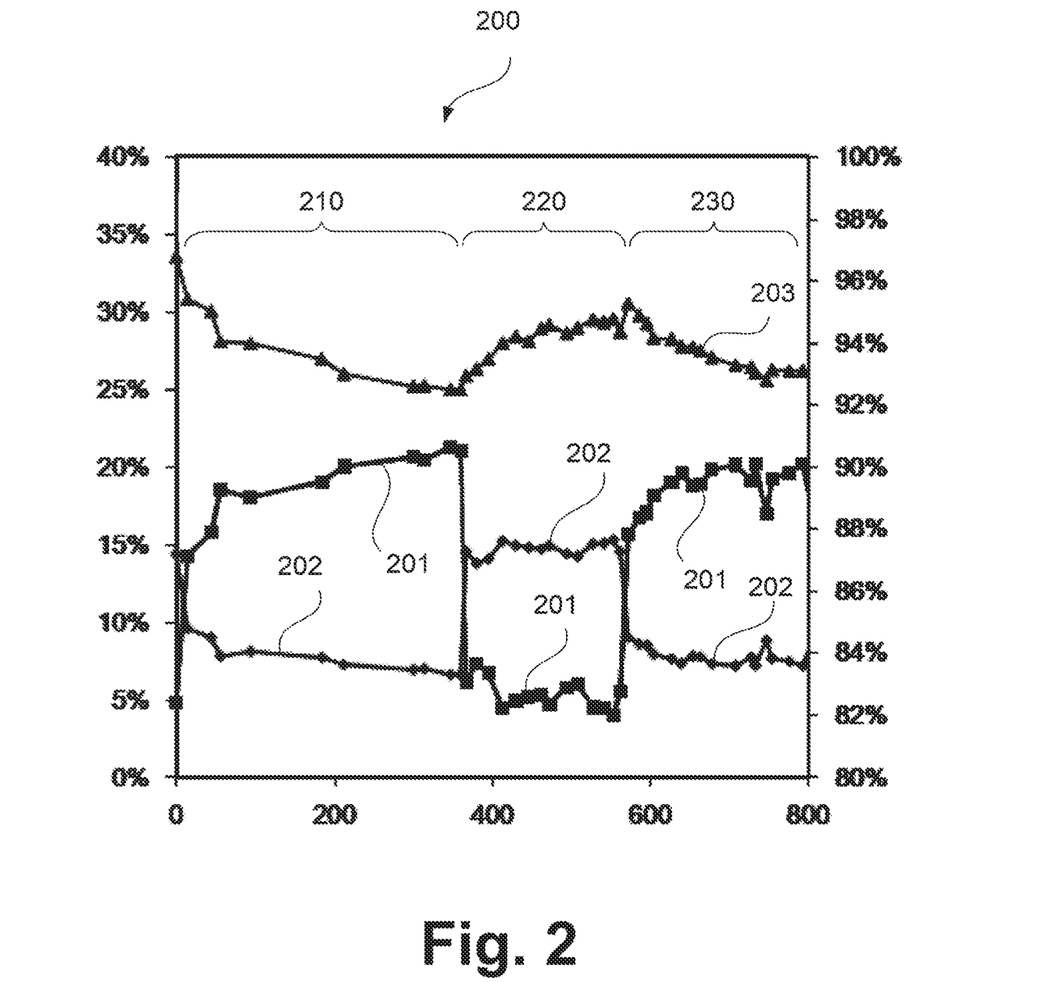
FIG. 2 shows the influencing of a catalyst activity by water which may be employed in the context of the present invention.

However, the present invention is based on precisely the converse finding. Thus in the context of the present invention a converse influence of the water content on the temperatures and the conversion in the reactor was found. The time-curve data shown for example in the accompanying FIG. 2 show how the increased metered addition of water increases the ethane conversion and increases the selectivity for acetic acid to approximately the same extent as it reduces the selectivity for ethylene. Since the reaction of ethane to afford acetic acid is more exothermic than that of ethane to afford ethylene, this is not a moderation of the reaction by water addition but precisely the converse. The water thus does not behave like a conventional diluent but rather is reaction-promoting. This catalyst behavior applies especially in the range for the water content mentioned as particularly preferable in the context of the present invention. An essential aspect of the present invention is accordingly that of exploiting this fact for the claimed controlling of the catalyst activity which may otherwise be influenced only with great difficulty.

As established in detail above, the catalyst activity may be controlled by adjustment of the water content in the reaction input stream. Reference is therefore made to the above intimations. Suitable variables indicating the activity of the catalyst which may be employed in the context of the present invention were also elucidated previously. Reference is also made to such variables hereinbelow.

In the context of the process according to the invention it may in particular be provided that the amount of the water in the reaction input stream is reduced when the at least one parameter indicates an activity of the catalyst above a predetermined value. Such a value may in particular be a suitable threshold value which is for example defined at a suitable distance from a value at which thermal runaway of a corresponding reactor must be expected. In particular on the basis of a repeated determination of the at least one parameter, a change over time, for example in the form of a trend, may be recognized and compared with a corresponding threshold value. If the threshold value is exceeded, a staged reaction may also be performed in which the amount of water is initially reduced only to a certain extent and later more severely reduced, for example to prevent steep gradients. The use of a plurality of such threshold values, from hysteresis functions, time increments and the like, is also possible.

In continuation of such a control step for avoiding thermal runaway in the process according to the invention the oxidative dehydrogenation using the catalyst may be performed in a reactor cooled with a cooling medium, wherein a temperature of the cooling medium is reduced after the amount of the water in the reaction input stream has been reduced. As mentioned previously for example to prevent thermal runaway, the reduction in the amount of water may constitute a first intervention step with rapid reaction time which is followed by the slower-reacting conventional steps, in particular using a cooling medium.

As mentioned, such a de-escalation for avoiding thermal runaway may also be continued, in particular by reducing the input. One embodiment of the invention thus provides for reducing at least one amount of the at least one paraffin in the reaction input stream after the amount of the water in the reaction input stream has been reduced. In this way the exothermicity may be reduced by reducing the amounts of reactant converted.

In largely analogous fashion to reducing the amount of the water in the reaction input stream when the at least one parameter indicates an activity of the catalyst above a predetermined value, an increase in the amount of the water in the reaction input stream may also be effected when the at least one parameter indicates an activity of the catalyst below a predetermined value. Here too, such a value may in particular be a suitable threshold value which is for example defined at a suitable distance from a value at which an excessively low conversion occurs. In particular here too on the basis of a repeated determination of the at least one parameter, a change over time, for example in the form of a trend, may be recognized and compared with a corresponding threshold value. Upon dropping below a corresponding threshold value here too a staged reaction may be performed in which the amount of water is initially increased only to a certain extent and later more severely increased, for example to prevent steep gradients. The use of a plurality of such threshold values, from hysteresis functions, time increments and the like, is also possible here.

In a particularly preferred embodiment of the present invention the at least one parameter is a parameter indicating the exothermicity of the oxidative dehydrogenation using the catalyst. By way of example a reactor temperature while maintaining a constant cooling output may be measured. For example a measurement inside a reactor or in the process gas (immediately) downstream of the reactor is possible. If such a temperature rises above, or falls below, a suitable threshold value, a reaction as previously elucidated may then be initiated. The advantages of such a control means compared to a conventional control means via cooling media has likewise been previously elucidated in detail.

In another advantageous embodiment, which may also be employed in combination with the embodiment elucidated just now, the at least one parameter is a parameter indicating the conversion of the at least one paraffin into one or more reaction products. As previously mentioned, and also elucidated with reference to FIG. 2, in particular the conversion of ethane in ODH-E under the corresponding respectively elucidated reaction conditions may be used as a measure for the catalyst activity.

In the context of the process according to the invention the amount of the water in the reaction input stream is in particular adjusted between 5 and 95 vol %, in particular 10 and 50 vol %, in particular 14 and 35 vol %. In other words a minimum amount of water is always provided which, as previously elucidated, ensures that the activity of the catalyst is maintained and does not decline due to lack of water. Compensation via a reactor temperature increase as described previously for classical processes is therefore not necessary. In an emergency, i.e. for a rapid reduction in the temperature, the amount of water may also be reduced to zero.

As mentioned, the present invention is employed in particular when in oxidative dehydrogenation a catalyst containing at least the elements molybdenum, vanadium, niobium and optionally tellurium, i.e. a so-called MoVTeNbO catalyst, is used because use of such a catalyst forms ethylene and acetic acid and a reaction system formed in this way behaves in the manner mentioned.

It is particularly advantageous when the oxidative dehydration is performed in the context of the present invention in a temperature range of 240° C. to 500° C. in a reactor bed of the reactor(s) used. In particular the temperature range may be 260° C. and 400° C., particularly preferably 280° C. to 350° C. The total pressure at the reactor inlet of the reactor(s) is preferably between 1 and 10 bar (abs.), in particular between 2 and 9 bar (abs.), more particularly between 3 and 8 bar (abs.). The space velocity in the reactor bed of the reactor(s) (WHSV) is in the range between 0.1 and 10 kg of ethane/(h×kg of catalyst), preferably between 0.5 and 5 kg of ethane/(h×kg of catalyst), particularly preferably between 0.7 and 3 kg of ethane/(h×kg of catalyst).

The process according to the invention may in particular be performed using one or more diluents that are added to the reaction input stream and pass into the process gas. The use of such diluents, which in particular ensure that during the strongly exothermic ODH a stable and safe reactor operation is guaranteed, is known in principle. As mentioned, to adjust the desired water content in the recited range, in particular an addition of water/water vapor into the reaction input stream may be effected. This water/this water vapor simultaneously acts as diluent. However, alternatively or in addition one or more further diluents may be used.

In particular, in the context of the present invention one or more diluents selected from the group consisting of water, methane, nitrogen and at least one further inert gas may be used. Carbon dioxide too may be used as diluent. Only a small proportion, if any, of such diluents take part in the reaction in the reactor(s) and therefore at least the predominant portion passes into the process gas.

The present invention also extends to a plant for producing an olefin which is adapted for forming a reaction input stream containing at least one paraffin, oxygen and water and which is further adapted for converting a portion of the paraffin and of the oxygen in the reaction input stream into the olefin by oxidative dehydrogenation using a catalyst to obtain a process gas, wherein the process gas contains at least the unconverted portion of the paraffin and of the oxygen, the olefin and the water from the reaction input stream. The plant features means adapted for determining at least one parameter which indicates an activity of the catalyst and a control unit which is adapted for adjusting an amount of the water in the reaction input stream on the basis of the at least one determined parameter.

For features and advantages of a corresponding plant, reference is made to the above elucidations concerning the features and advantages of the process. In particular such a plant is adapted for performing a process according to the specific embodiments elucidated above and comprises means suitable therefor. In this regard too, reference is made to the above intimations.

The invention is more particularly elucidated below with reference to the appended drawings which illustrate inter alia preferred embodiments of the present invention.

DETAILED DESCRIPTION OF THE DRAWINGS

In the figures that follow, functionally or structurally equivalent elements are indicated with identical reference numerals and for the sake of simplicity are not repeatedly elucidated. When plant parts are described hereinbelow the elucidations concerning these also apply correspondingly to the process steps implemented by means of these plant parts and vice versa.

Figure 1:
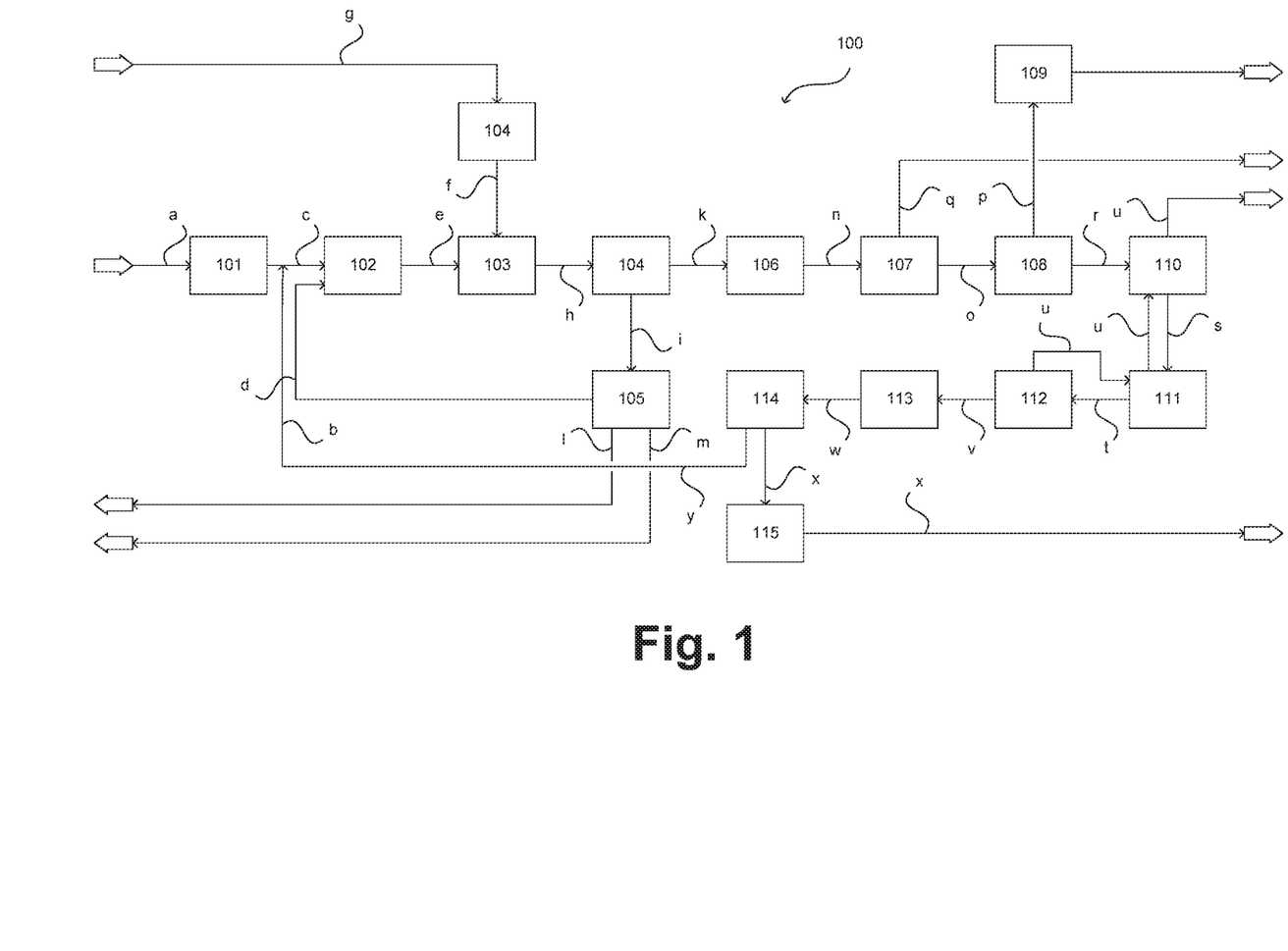
FIG. 1 shows a plant for producing ethylene and acetic acid according to one embodiment of the invention.

In FIG. 1 a plant for producing olefins according to one embodiment of the invention in the form of a greatly simplified plant diagram is illustrated and collectively referred to as 100. Notwithstanding that a plant 100 for ODH of ethane (ODH-E) is described below, the present invention is also suitable, as recited, for use in ODH of higher hydrocarbons. In this case the elucidations which follow apply correspondingly.

In the plant 100 a separation input in the form of a material stream a is supplied to a rectification unit 101 having for example one or more rectification columns and subjected to a rectification. In the depicted example the separation input contains at least ethane and higher hydrocarbons, in particular corresponding higher paraffins. The rectification unit 101 may also be supplied with one or more further separation inputs, for example the material stream b shown here and more particularly elucidated below.

In the rectification unit 101 the separation input is subjected to a rectification alone or together with the further separation input(s) to obtain a gas mixture which contains ethane but is poor in higher hydrocarbons. The gas mixture is withdrawn in the form of a material stream c and supplied to a preheating unit 102. In the preheating unit 102 the gas mixture is preheated, wherein in the depicted example the preheating unit 102 is also supplied with a water or steam stream d. Further material streams may also be supplied, as is illustrated here in the form of a material stream b. Further obtained in the rectification unit 101 is a component mixture containing predominantly or exclusively the higher hydrocarbons. Said mixture is not shown explicitly.

A material stream e outflowing from the preheating unit 102 is supplied to a reaction unit 103 to form a reaction input stream. On account of its formation using the separated product from the rectification unit 101 the reaction input stream contains ethane but is poor in higher hydrocarbons. The reaction input stream may further contain one or more diluents such as water or inert gases and further components. These may also be supplied to the reaction unit 103 in the form of further material streams (not shown).

In the depicted example the reaction unit 103 is supplied with an oxygen-containing material stream f. This may be provided using an air separation plant 104. To this end the air separation plant 104 is supplied with an airstream g. The oxygen-containing material stream f may be substantially pure oxygen but fractions of nitrogen and of noble gases may also be present depending on the operation of the air separation plant 104. In this way it is likewise possible to supply diluent.

Outflowing from the reaction unit 103 is a process gas in the form of a process gas stream h which contains ethylene formed in the reaction unit 103 by ODH of a portion of the ethane in the reaction input stream. The product mixture further contains acetic acid likewise formed from ethane during ODH in the reaction unit 103, water, carbon monoxide, carbon dioxide, unconverted oxygen and the diluent(s) and further compounds if added or previously formed in the reaction unit 103.

It will be appreciated that reaction unit 103 may comprise a or else a plurality of reactors which are for example operated in parallel. In the latter case these reactors are each supplied with corresponding reaction inputs, which may have identical or different compositions, and corresponding oxygen-containing material streams f, and in each case corresponding process gas streams h are formed. The latter may for example be combined and supplied together as process gas to the units elucidated below.

The process gas is transferred into a quench unit 104 in which, for example in a quench column, it may be contacted with quench water or a suitable aqueous solution. In the quench unit 104 the process gas is in particular cooled and the acetic acid formed in the reaction unit 103 is scrubbed out of the process gas. Acetic acid-laden process water outflows from the quench unit 104 in the form of a material stream i, the process gas at least largely freed of acetic acid outflows from the quench unit 104 in the form of a material stream k.

In an optional acetic acid recovery unit 105 acetic acid is separated off from the acetic acid-laden process water as glacial acetic acid which is discharged from the plant 100 as material stream l. Pure process water likewise recovered in the acetic acid recovery unit 105 may be supplied to the preheating unit 102 in the form of the previously elucidated material stream d. The process water supplied to the reactor may also be provided partly or fully in the form of externally supplied freshwater. Water that is no longer usable or required may be discharged from the plant 100 and supplied to a wastewater treatment in the form of a wastewater stream m.

The process gas present in the form of material stream k and at least largely freed of acetic acid is compressed to a suitable pressure level, for example 15 to 25 bar, in a compressing unit 106 and in the form of a compressed material stream n supplied to an amine scrub unit 107. Scrubbed out therein are in particular portions of the carbon dioxide present in the process gas. After regeneration of the amine the scrubbed-out carbon dioxide may be discharged from the plant in the form of a material stream q. The process gas thus partly freed of carbon dioxide is transferred in the form of a material stream o into a lye scrub unit 108 and further purified of carbon dioxide therein. Generated in the lye scrub unit 108 is waste lye which in the form of a material stream p may be transferred into a waste lye treatment unit 109 and finally discharged from the plant 100.

The process gas further purified in the lye scrub unit 108 is transferred in the form of a material stream r into a pre-cooling and drying unit 110 where it may be freed from residual water in particular. The dried process gas is transferred in the form of a material stream s into a low temperature unit 111 and subsequently in further-cooled form in the form of one or more material streams t into a demethanization unit 112. In the low temperature unit 111 and the demethanization unit 112 components lower boiling than ethylene, in particular carbon monoxide and oxygen, are separated off from the process gas, wherein the remainder stays in condensed form. If the process gas contains higher hydrocarbons formed as a byproduct during ODH in the reaction unit 103 these are likewise converted into the condensate.

The separated-off components lower boiling than ethylene are recycled in the form of one or more material streams u through the low temperature unit 111 and the precooling and drying unit 110, therein optionally combined with further corresponding material streams, used for cooling purposes and discharged from the plant 100. If required the hydrocarbons having two and optionally more carbon atoms are supplied in the form of a material stream v to a hydrogenation unit 113 in which in particular acetylene likewise formed as byproduct during ODH in the reaction unit 103 may be hydrogenated. After the hydrogenation the material stream now referred to as w is transferred into an ethylene removal unit 114.

In the ethylene removal unit 114 ethylene is at least largely separated off from other components and in the form of a material stream x after utilization in an ethylene cooling unit 115 may be discharged from the plant 100 in gaseous form. The remaining components, predominantly ethane and optionally higher hydrocarbons, are withdrawn in the form of a material stream y. If higher hydrocarbons are present therein these are advantageously recycled into the reaction unit in the form of the previously recited material stream b. An optional workup of this material stream b may be effected.

Through an adapted operation of the ethylene removal unit 114/a corresponding configuration, a portion of the ethylene may also be passed into material stream y/b and recycled into the process therein. It is also possible to recycle the material stream x or a portion thereof. In this way it is possible to increase the yield of acetic acid if required and thus adapt the selectivity. It is expressly emphasized that in the context of the present invention certain plant parts, in particular for example the rectification unit 101, may be eschewed. In this case the material stream y may for example also be introduced directly into the preheating unit 102 or into the reaction unit 103. Further variants are possible and encompassed by the present invention.

FIG. 2 shows the influencing of a catalyst activity by water which may be employed in the context of the present invention with reference to a diagram 200. Diagram 200 shows the results of an experiment as elucidated previously and described once again hereinbelow.

In diagram 200 a selectivity for acetic acid and a conversion of ethane are plotted on the left ordinate and a selectivity for ethylene is plotted on the right ordinate in each case in percent against time in minutes along the abscissa. The development of the selectivity for ethylene over time is shown in the form of a graph 201 and that for acetic acid in the form of a graph 202. The development of the conversion of ethane is depicted in the form of a graph 203.

The experiment was effected at a space velocity of 1.19 kg of ethane/(h×kg of catalyst) and a fixed molar ratio of ethane to oxygen of 4 in the reactor input. For the experiment 48.8 g of undiluted catalyst were filled into a laboratory reactor having an internal diameter of 10 mm.

In the depicted experiment after a first "dry" operating period 210 during which no water was added into the reaction input stream, the water content in the reaction input stream was initially instantaneously increased from 0 to 22 vol %, during an operating period 220 maintained at this value and then instantaneously reduced back to 0 vol % and during an operating period 230 in turn maintained at this value.

It is apparent that after addition of water the catalyst activity (here in the form of ethane conversion, graph 203) increases rapidly and in the further course of the operating period 220 further increases slightly. Upon removal of the water a rapid short-term drop in activity followed further by a continuous reduction over the operating period 230 is once again observed. For these changes in water content a step change in the selectivities (for ethylene and acetic acid, graphs 201 and 202) occurs simultaneously. Upon addition of water, the product selectivity is shifted virtually instantaneously toward more acetic acid, upon removal of the water toward more ethylene.

The invention claimed is:

1. Process for producing an olefin in which a reaction input stream containing at least one paraffin, oxygen and water, is formed and in which a portion of the paraffin and of the oxygen in the reaction input stream is converted into the olefin by oxidative dehydrogenation using a catalyst to obtain a process gas, wherein the process gas contains at least the unconverted portion of the paraffin and of the oxygen, the olefin and the water from the reaction input stream, characterized in that at least one parameter is determined and that an amount of the water in the reaction input stream is adjusted on the basis of the at least one determined parameter, wherein said at least one parameter is acitvity of the catalyst.

2. Process according to claim 1 in which the amount of the water in the reaction input stream is reduced when the at least one parameter indicates an activity of the catalyst above a predetermined value.

3. Process according to claim 2 in which the oxidative dehydrogenation using the catalyst is performed in a reactor cooled with a cooling medium, wherein a temperature of the cooling medium is reduced after the amount of the water in the reaction input stream has been reduced.

4. Process according to claim 2 in which at least an amount of the oxygen in the reaction input stream is reduced after the amount of the water in the reaction input stream has been reduced.

5. Process according to claim 2 in which at least an amount of the at least one paraffin in the reaction input stream is reduced after the amount of the water in the reaction input stream has been reduced.

6. Process according to claim 1 in which the amount of the water in the reaction input stream is increased when the at least one parameter indicates an activity of the catalyst below a predetermined value and/or when the at least one parameter indicates a fall in an activity of the catalyst over time.

7. Process according to claim 1 in which the at least one parameter is a parameter indicating the exothermicity of the oxidative dehydrogenation using the catalyst, a parameter indicating the conversion of the at least one paraffin into one or more reaction products and/or a temperature in a reactor employed for the oxidative dehydrogenation or downstream of this reactor.

8. Process according to claim 1 in which the amount of the water in the reaction input stream is adjusted between 5 and 95 vol %, in particular 10 and 50 vol %, in particular 14 and 35 vol %.

9. Process according to claim 1 in which the oxidative dehydrogenation is performed at a temperature of the catalyst in a range between 240° C. and 500° C.

10. Process according to claim 1 in which one or more reactors are used for the oxidative dehydrogenation and in which the total pressure of the reaction input stream at the inlet of the reactor(s) is in a range between 1 and 10 bar (abs.).

11. Process according to claim 1 in which the oxidative dehydrogenation is performed at a space velocity in a range between 0.1 and 10 kg of ethane/(h×kg of catalyst).

12. Process according to claim 1 in which one or more diluents that pass into the process gas are further added to the reaction input stream.

13. Process according to claim 12 in which the diluent(s) is or are selected from the group consisting of methane, nitrogen, carbon dioxide and at least one further inert gas.

14. Process according to claim 1, wherein the catalyst used contains at least the elements molybdenum, vanadium, niobium and optionally tellurium.

15. Plant (100) for producing an olefin which is adapted for forming a reaction input stream containing at least one paraffin, oxygen and water and which is further adapted for converting a portion of the paraffin and of the oxygen in the reaction input stream into the olefin by oxidative dehydrogenation using a catalyst to obtain a process gas, wherein the process gas contains at least the unconverted portion of the paraffin and of the oxygen, the olefin and the water from the reaction input stream characterized by means adapted for determining at least one parameter which indicates an activity of the catalyst and by a control unit which is adapted for adjusting an amount of the water in the reaction input stream on the basis of the at least one determined parameter.

16. Process according to claim 3 in which at least an amount of the oxygen in the reaction input stream is reduced after the amount of the water in the reaction input stream has been reduced.

17. Process according to claim 3 in which at least an amount of the at least one paraffin in the reaction input stream is reduced after the amount of the water in the reaction input stream has been reduced.

18. Process according to claim 4 in which at least an amount of the at least one paraffin in the reaction input stream is reduced after the amount of the water in the reaction input stream has been reduced.

19. Process according to claim 2 in which the amount of the water in the reaction input stream is increased when the at least one parameter indicates an activity of the catalyst below a predetermined value and/or when the at least one parameter indicates a fall in an activity of the catalyst over time.

20. Process according to claim 3 in which the amount of the water in the reaction input stream is increased when the at least one parameter indicates an activity of the catalyst below a predetermined value and/or when the at least one parameter indicates a fall in an activity of the catalyst over time.

* * * * *